US00PP20821P2

(12) United States Plant Patent
Pedersen

(10) Patent No.: US PP20,821 P2
(45) Date of Patent: Mar. 9, 2010

(54) ***CAMPANULA* PLANT NAMED 'ROYAL'**

(50) Latin Name: *Campanula portenschlagiana*
Varietal Denomination: ROYAL

(75) Inventor: Jens Ingemann Pedersen, Odense (DK)

(73) Assignee: Gartneriet Tvillingegaarden A/S, Odense (DK)

( * ) Notice: Subject to any disclaimer, the term of this patent is extended or adjusted under 35 U.S.C. 154(b) by 0 days.

(21) Appl. No.: 12/316,820

(22) Filed: Dec. 17, 2008

(51) Int. Cl.
*A01H 5/00* (2006.01)

(52) U.S. Cl. ..... Plt./414

(58) Field of Classification Search ..... Plt./263, Plt./414

See application file for complete search history.

(56) References Cited

OTHER PUBLICATIONS

Print out of Danish Gazettes for Plant Varieties for corresponding, international PBR application, No. 22847, filed Apr. 11, 2005, with Breeder's Reference No. JLK KLON-8 (see Gazette dated Jul. 15, 2005, p. 35, 3 pages), and granted as Registration No. 22847 on Aug. 1, 2008 with approved Variety Denomination 'Royal' (see Gazette dated Sep. 1, 2008, p. 80, 3 pages).
Print out of EU-CPVO Gazette Extract for corresponding, international PBR application, No. 2008/1959 filed Sep. 8, 2008, with proposed Variety Denomination 'Royal', 4 pages. (www.cpvoextranet.cpvo.europa.eu, Dec. 16, 2008).

*Primary Examiner*—Susan B McCormick Ewoldt
(74) *Attorney, Agent, or Firm*—Foley & Lardner LLP

(57) ABSTRACT

A new distinct cultivar of *Campanula* plant named 'ROYAL', characterized by its upright, compact, rounded plant habit; plant spread measuring about 22 cm; purple-violet colored mature petals (upper surface: RHS N82B); green colored mature leaves (upper surface: RHS N137A); cordate leaves with an acute tip; short internode measuring about 11 mm; and sepal texture that is dull, with short stiff hair on margin with abaxial side.

4 Drawing Sheets

Botanical designation: *Campanula portenschlagiana.*
Variety denomination: 'ROYAL'.

BACKGROUND OF THE INVENTION

The present invention relates to a new and distinct cultivar of *Campanula* plant, botanical known as *Campanula portenschlagiana* Schult., commonly known as Dalmatian Bellflower, and hereinafter referred to by the name 'ROYAL'.

The new *Campanula* 'ROYAL' is a product of a planned breeding program conduced by the inventor, Jens Ingemann Pedersen, in Odense, Denmark. The objective of the breeding program is to develop a new *Campanula* cultivar with compact growth habit, large flowers and darker green leaves.

The new *Campanula* originated from a cross made in a controlled breeding program made by the inventor in 2002 in Odense, Denmark. The female or seed parent is *Campanula portenschlagiana* Schult. 'MONIC' (unpatented). The male parent or pollen parent is an unknown, unpatented *Campanula portenschlagiana* Schult. cultivar. The new *Campanula* 'ROYAL' was discovered and selected by the inventor as a single flowering plant within the progeny of the stated cross in February of 2005 in a controlled environment in Odense, Denmark. The inventor selected 'ROYAL' on the basis of its compact plant habit and flowering habit.

Asexual reproduction of the new *Campanula* cultivar by vegetative cuttings was first performed in April of 2005 in Odense, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits has been repeatedly observed and are determined to be unique characteristics of 'ROYAL'. These characteristics in combination distinguish this *Campanula* as a new and distinct cultivar:

1. Upright, compact, rounded plant habit;
2. Plant spread measuring about 22 cm;
3. Purple-violet colored mature petals (upper surface: RHS N82B);
4. Green colored mature leaves (upper surface: RHS N137A);
5. Codate leaves with an acute tip;
6. Short internode measuring about 11 mm; and
7. Sepal texture that is dull, with short stiff hair on margin and abaxial side.

Plants of the new *Campanula* 'ROYAL' differ from the female or seed parental cultivar, *Campanula* 'MONIC' (unpatented) in the characteristics described in Table 1.

TABLE 1

| Characteristics | New Cultivar 'ROYAL' | Female Parent 'MONIC' (unpatented) |
|---|---|---|
| Plant size | Compact | Medium |
| Plant growth | Vigorous | Medium |
| Flower size | Large | Medium |
| No. of flowers per plant | Very many flowers | Many flowers |
| Leaf color upper surface | Green | Grayish green |
| Leaf size | Small | Large |

Of the many commercial cultivars known to the inventor, the most similar in comparison to the new *Campanula* 'ROYAL' is the *Campanula portenschlagiana* Schult. 'PKMP01' (patented, U.S. Plant Pat. No. 17,205) and *Campanula portenschlagiana* Schult. 'PKMP05' (patented, U.S. Plant Pat. No. 17,188), in the characteristics described in Table 2.

TABLE 2

| Characteristics | New Cultivar 'ROYAL' | 'PKMP01' (U.S. Plant Pat. No. 17,205) | 'PKMP05' (U.S. Plant Pat. No. 17,188) |
|---|---|---|---|
| Petal color (when fully opened): | Upper surface: Purple-violet, RHS N82B Lower surfaces: Purple-violet, RHS N82C | Upper surface: Violet, RHS N87B Lower surface: Violet, RHS N87C | Upper surface: Violet, RHS N87A Lower surface: Violet, RHS N88D |
| Mature leaf color: | Upper surface: Green, RHS N137A | Upper surface: Green, RHS N139C | Upper surface: Green, RHS N138A |
| Leaf tip shape: | Acute | Broad acuminate | Rounded |
| Sepal texture: | Dull, short stiff hair on margin and abaxial side | Shiny and glabrous | Shiny and glabrous |
| Plant diameter or spread: | About 22 cm | 23 cm to 27 cm | About 27 cm |

BRIEF DESCRIPTION OF THE PHOTOGRAPHS

The accompanying colored photographs drawings illustrate the overall appearance of the new *Campanula* 'ROYAL', showing the colors as true as is reasonably possible with colored reproductions of this type. Colors in the photographs may differ slightly from the color values cited in the detailed botanical description, which more accurately describe the actual colors of 'ROYAL'.

DETAILED BOTANICAL DESCRIPTION

Figure 1:
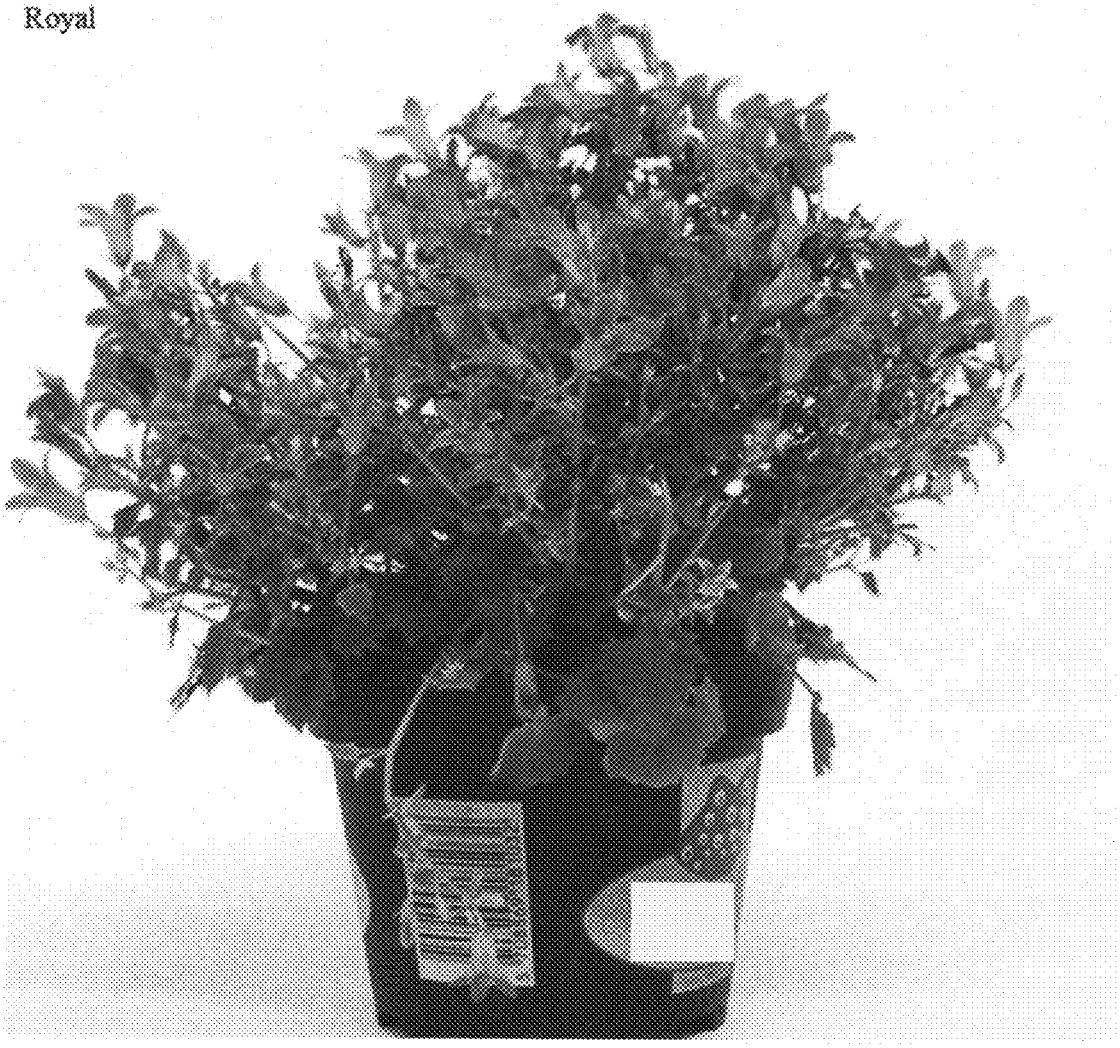
FIG. 1 shows a side perspective view of a typical flowering plant of 'ROYAL', as grown in 11 cm pots at about 16 to 20 weeks after cutting.
Figure 2:
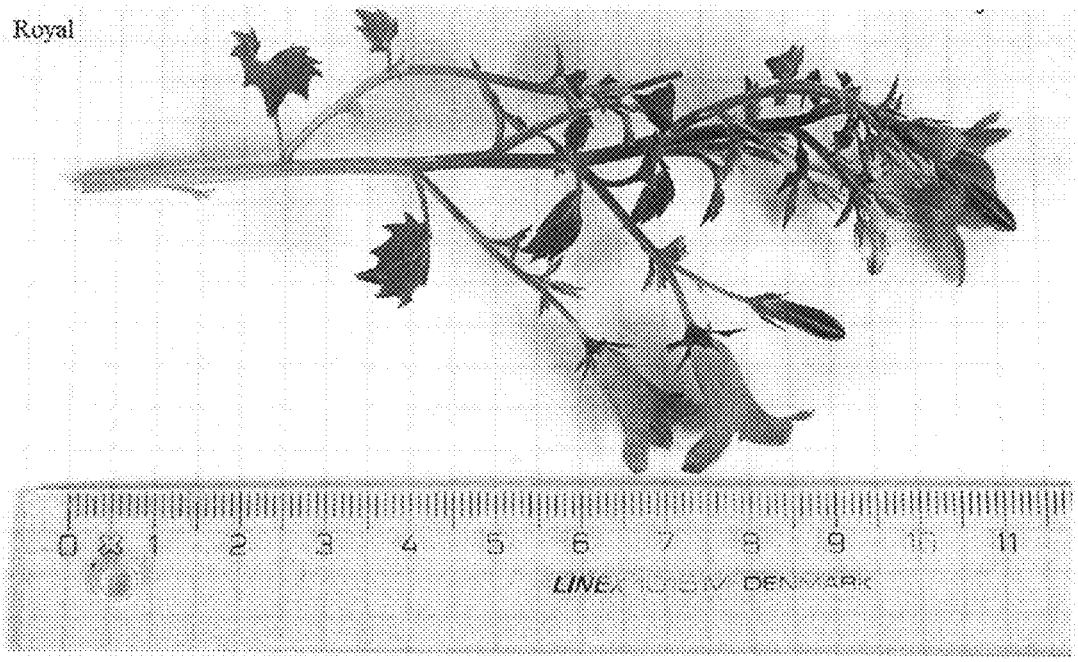
FIG. 2 shows a close-up view of a typical branch with leaves and flowers in a raceme of 'ROYAL' at about 16 to 20 weeks after cutting.
Figure 3:
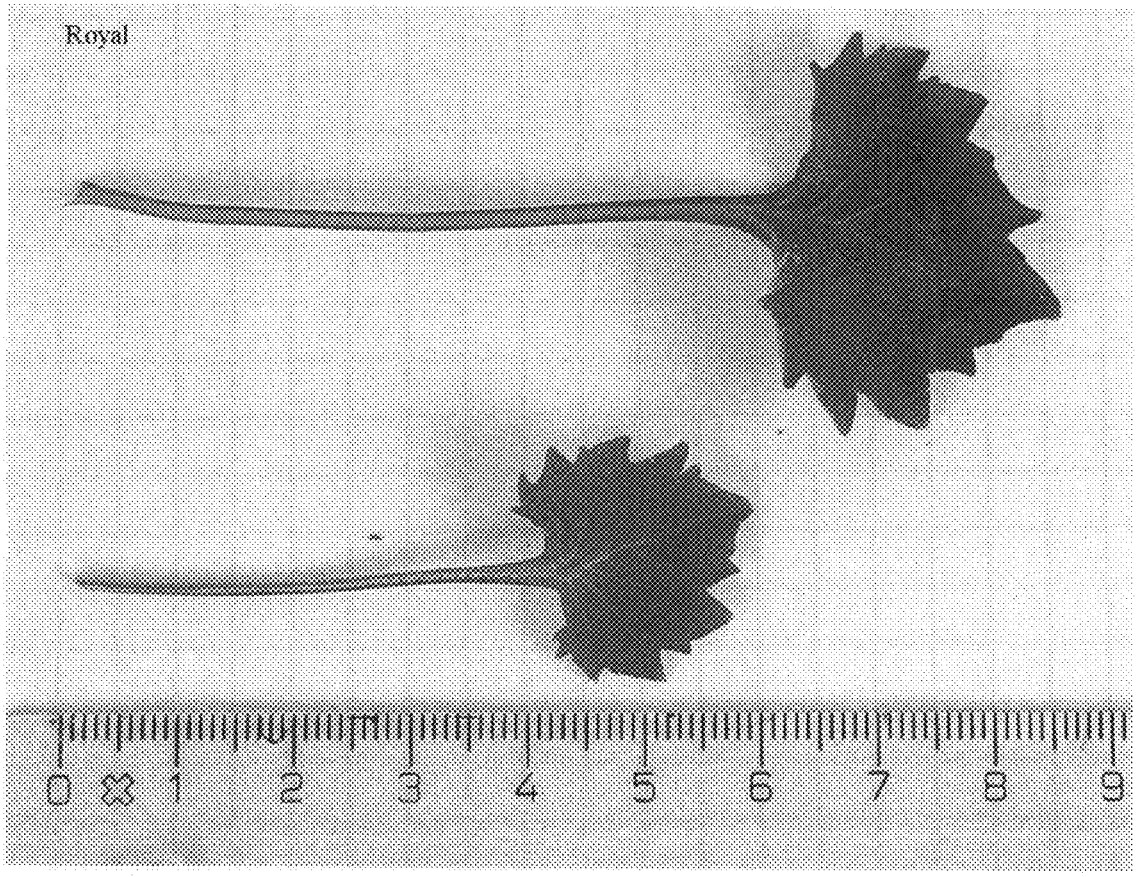
FIG. 3 shows a close-up view of typical leaves produced by 'ROYAL' at about 16 to 20 weeks after cutting.
Figure 4:
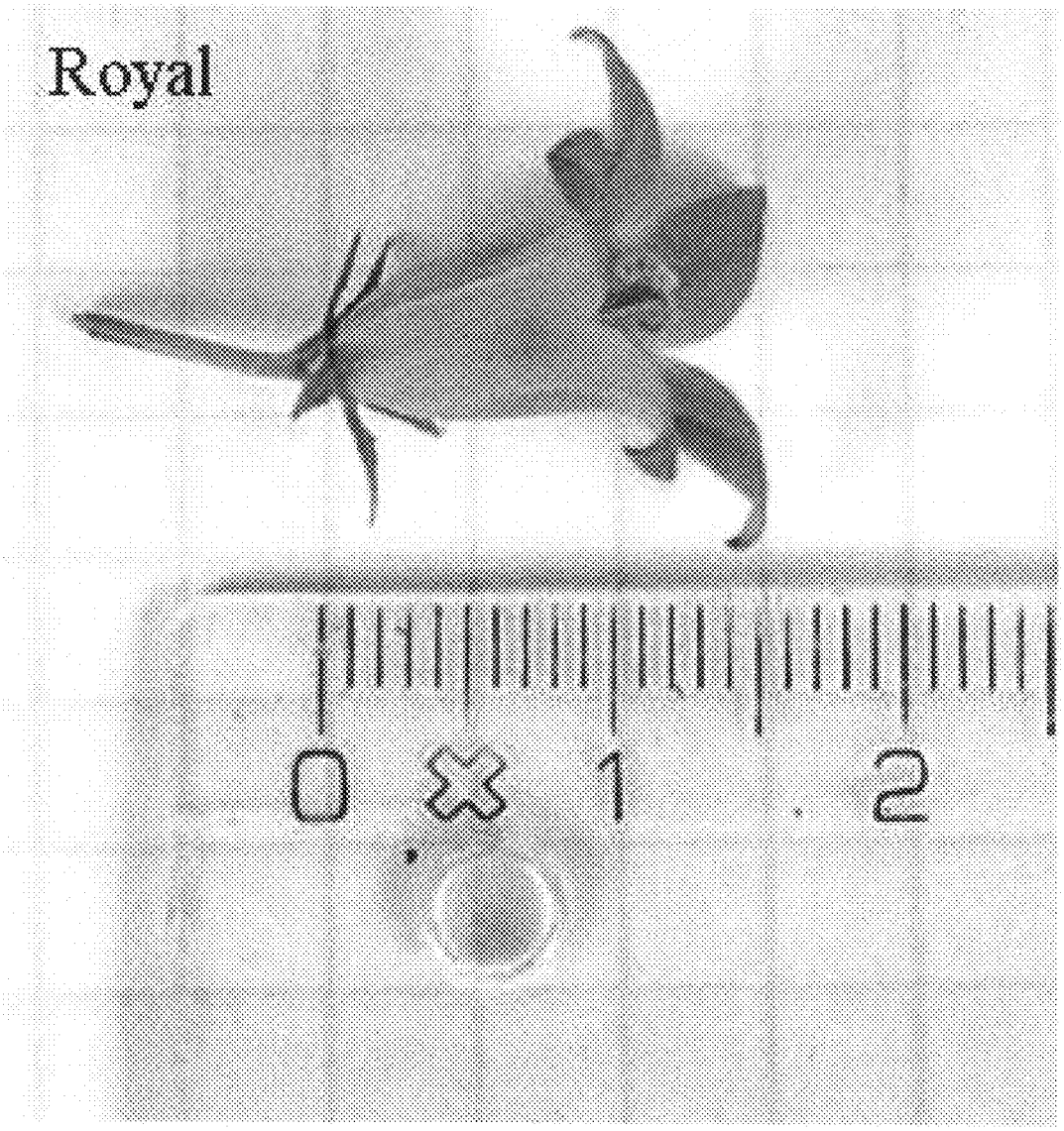
FIG. 4 shows a close-up view of a single flower produced by 'ROYAL' at about 16 to 20 weeks after cutting.

The new *Campanula* 'ROYAL' have not been observed under all possible environmental conditions. The phenotype of the new cultivar may vary with variations in environment such as temperature, light intensity, day length, and fertility level without any change in the genotype of the plant.

The aforementioned photographs, together with the following observations, measurements and values describe plants of the new *Campanula* 'ROYAL' as grown in a heated and lighted glass-covered greenhouse in Odense, Denmark under conditions which closely approximate those generally used in commercial practice. Plants of 'ROYAL' were grown under day temperatures ranging from 18° C. to 22° C. and a night temperature average of 18° C. Plants of 'ROYAL' are grown using ambient light levels of +45WM$^2$ and 15 hour long photoperiodic treatments. No growth retardants are used.

Color references are made to The Royal Horticultural Society Colour Chart (R.H.S.), 5$^{th}$ Edition, 2007, except where the general colors of ordinary significance are used. The age of the plants described is about 16 to 20 weeks old after cutting, as grown in 11 cm pots.

Classification:

*Botanical.*—*Campanula portenschlagiana* Schult.

Parentage:

*Female or seed parent.*—*Campanula portenschlagiana* Schult. 'MONIC' (unpatented).

*Male or pollen parent.*—Unknown, unpatented *Campanula portenschlagiana* Schult. seedling.

Propagation:

*Type.*—Vegetative cuttings.

*Time to initiate roots.*—About 3–4 weeks at 18° C. to 21° C. in tunnels in a greenhouse.

*Root description.*—Fine, well branched, fibrous.

Plant:

*Form.*—Perennial, herbaceous plant with upright, compact plant habit and overall rounded shape. Produced as potted plant. Campanulate flowers in racemes. Freely branching with lateral branches forming at every node; dense and bushy.

*Crop time.*—After rooting about 12 to 16 weeks are required to produce finished flowering plants in 11 cm pots.

*Vigor.*—Vigorous growth rate.

*Size.*—Height (soil level to top of plant plane): About 10 cm to 14 cm. Spread: About 22 cm.

*Stem.*—Shape: Round. Strength: Moderately strong. Aspect: Upright and spreading. Texture: Smooth with short stiff hair, shiny. Color: RHS 146B, yellow-green.

*Lateral branches.*—Habit: Freely branching. Basal spreading branches and central upright stem when flowering. No pinching required. Quantity: About 60 to 65 per plant. Leaves per lateral branch: About 6. Average length: 11 cm to 12 cm (including flowers). Branch diameter: 1 mm to 2 mm. Internode length: 11 mm.

Foliage:

*Type.*—Leaves single and alternate, cordate in overall shape, dentate margin, palmate venation.

*Length.*—15 mm to 25 mm.

*Width.*—20 mm to 30 mm.

*Shape.*—Cordate.

*Apex.*—Acute.

*Base.*—Cordate.

*Margin.*—Broadly dentate.

*Texture* (*both surfaces*).—Smooth, dull.

*Pubescence.*—Short stiff hair on the abaxial side and along veins and margin.

*Color.*—Young foliage: Upper surface: RHS 137A, green Lower surface: RHS N138B, green. Mature foliage: Upper surface: RHS N137A, green; Lower surface: RHS N138B, green.

*Venation.*—Pattern: Palmate. Color: Upper surface: RHS 137B, green. Lower surface: RHS 138B, green.

*Petiole.*—Length: 3 cm to 6 cm. Diameter: 1 mm to 2 mm. Texture: Smooth with short stiff hairs. Color: RHS 137B, green.

Inflorescence description:

*Flower arrangement and shape.*—Single, upright flowers in racemes; campanulate flowers with small star shaped calyx.

*Natural flowering season*.—Continuous throughout the spring and summer. Season can be extended by long day treatments.

*Time to flower*.—About 8 to 12 weeks after planting of rooted cutting.

*Flower longevity on the plant*.—About 10 to 14 days. Longevity of individual flowers is highly dependent on temperature and light conditions. Flowers persistent.

*Inflorescence size*.—Height: About 10 cm Diameter: About 20 cm.

*Number of flowers per inflorescence*.—About 3 to 4.

*Number of flowers per lateral stem*.—About 15 to 20.

*Number of flowers and buds per plant*.—About 900 to 1300.

*Buds*.—Length: Up to 15 mm. Diameter: Up to 3 mm. Shape: Oblong, ridged. Rate of opening: About 1 to 3 per day. Color: White-green to RHS 86B, violet.

*Petals*.—Quantity per flower: 5. Arrangement: Single, sympetalous; bell-shaped, basally fused campanulate; persistent. Overall shape: Bell-shaped, campanulate. Apex: Acute. Base: Fused. Margin: Margin. Length: 7 mm to 9 mm. Width: 5 mm. Texture: Velvety. Color (when opening): Upper surfaces: RHS N82B, purple-violet; Lower surfaces: RHS N87C, violet. Color (when opened): Upper surfaces: RHS N82B, purple-violet; Lower surfaces: RHS N82C, purple-violet.

*Sepals*.—Quantity per flower: 5. Arrangement: Dull, free. Overall shape: Arrow-shape. Apex: Cuspidate. Base: Fused. Length: 5 mm. Width: 1 mm. Margin: Entire. Color (immature and mature): Upper and lower surfaces: RHS 143A, green. Texture: Dull. Pubescence: Short stiff hairs on margin and the abaxial side.

*Peduncle*.—Strength: Moderately strong. Length: About 25 mm to 35 mm. Diameter: About 1–2 mm. Color: RHS 146B, yellow-green.

*Pedicels*.—Angle: Acute. Length: About 10 mm to 15 mm. Diameter: About 1 mm. Strength: Moderately strong. Color: RHS 146B, yellow-green.

Reproductive organs:

*Androecium*.—Stamen: Quantity per flower: 5; fused, until pollen is shed. Anther: Shape: Fused. Diameter: 1 mm. Color: RHS 155A, white. Pollen: Amount: Moderate. Color: RHS 155A, white.

*Gynoecium*.—Pistil: Quantity per Flower: 1. Length: About 14 mm. Stigma: Shape: Tripartite. Color: RHS 90B, violet-blue. Style: Length: About 10 mm. Color: RHS 90C, violet-blue. Ovary: Color: RHS 144C, yellow-green.

Seed/fruit: None observed.

Disease/pest resistance: None observed.

Disease/pest susceptibility: 'ROYAL' is susceptible to botrytis.

Weather tolerance: Plants of the new *Campanula* have exhibited good tolerance to drought, rain and wind, with low temperature resistance to −20° C.

I claim:

1. A new and distinct cultivar of *Campanula* plant named 'ROYAL', as described and illustrated and described herein.

* * * * *